US007341988B2

(12) United States Patent
Nishizono et al.

(10) Patent No.: US 7,341,988 B2
(45) Date of Patent: Mar. 11, 2008

(54) METHOD OF TREATING INFLUENZA WITH GERANYL-GERANYL ACETONE

(75) Inventors: Akira Nishizono, Hasama-machi (JP); Masako Unoshima, Hasama-machi (JP); Hideo Iwasaka, Hasama-machi (JP); Takayuki Noguchi, Hasama-machi (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 129 days.

(21) Appl. No.: 10/493,460

(22) PCT Filed: Oct. 24, 2002

(86) PCT No.: PCT/JP02/11060

§ 371 (c)(1), (2), (4) Date: Aug. 23, 2004

(87) PCT Pub. No.: WO03/035052

PCT Pub. Date: May 1, 2003

(65) Prior Publication Data
US 2004/0265319 A1 Dec. 30, 2004

(30) Foreign Application Priority Data
Oct. 25, 2001 (JP) ............................. 2001-327823

(51) Int. Cl.
*A61K 39/145* (2006.01)
(52) U.S. Cl. ........................................ 514/1; 424/206.1
(58) Field of Classification Search ...................... None
See application file for complete search history.

(56) References Cited

U.S. PATENT DOCUMENTS
2004/0249219 A1* 12/2004 Saucy ........................ 568/388

FOREIGN PATENT DOCUMENTS
JP 2001-213770 8/2001
WO WO 02/098398 A1 12/2002

OTHER PUBLICATIONS

Yamagami et al. Effects of geranyl-geranyl-acetone administration before heat shock preconditioning for conferring tolerance against ischemia-reperfusion injury in rat livers, J. Lab. Clin. Med. (2000) 135:465-475.*
Pavlovic et al., J. Virology, 1992, 66(4):2564-2569.*
Unoshima et al. Antimicrobial Agents and Chemotherapy, 2003, 47(9) :2914-2921.*
Inoue et al. Antimicrobial Agents and Chemotherapy, May 2005, 49(5):1770-1774.*
Encyclopedia of Alternative Medicine, "Boneset", Belinda Rowland, Apr. 6, 2001, internet print out is three pages.*
JPO/NCIPI unverified English language translation of document AL1, JP 2001-213770.

Conti, C., et al., "Antiviral Effects of Hyperthermic Treatment in Rhinovirus Infection," *Antimicrobial Agents Chemother.* 43:822-829, American Society for Microbiology (1999).
Couch, R.B., et al., "Influenza: Its Control in Persons and Populations," *J. Infect. Dis.* 153:431-440, The University of Chicago Press (1986).
Glezen, W.P., "Serious Morbidity and Mortality Associated with Influenza Epidemics," *Epidemiol. Rev.* 4:25-44, The Johns Hopkins University Press (1982).
Gubareva, L.V., et al., "Influenza virus neuraminidase.inhibitors," *Lancet* 355:827-835, Lancet Publishing Group (Mar. 2000).
Hayden, F.G., et al., "Efficacy and Safety of the Neuraminidase Inhibitor Zanamivir in the Treatment of Influenzavirus Infections," *N. Engl. J. Med.* 337:874-880, Massachusetts Medical Society (1997).
Hirakawa, T., et al., "Geranylgeranylacetone Induces Heat Shock Proteins in Cultured Guinea Pig Gastric Mucosal Cells and Rat gastric Mucosa," *Gastroenterology* 111:345-357, W.B Saunders Company (1996).
Long, J.K., et al., "Antiviral agents for treating influenza," *Cleve. Clin. J. Med.* 67:92-95, Cleveland Clinic Educational Foundation (Feb. 2000).
Wingfield, W.L., et al., "Therapeutic Efficacy of Amantadine HCI and Rimantadine HCI in Naturally Occurring Influenza A2 Respiratory Illness in Man," *N. Engl. J. Med.* 281:579-584, Massachusetts Medical Society (1969).
Woods, J.M., et al., "4-Guanidino-2,4-Dideoxy-2,3-Dehydro-*N*-Acetylneuraminic Acid is a Highly Effective Inhibitor Both of the Sialidase (Neuraminidase) and of Growth of a Wide Range of Influenza A and B Viruses In Vitro," *Antimicrobial Agents Chemother.* 37:1473-1479, American Society for Microbiology (1993).
The Advisory Committee of Immunization Practices, "Prevention and Control of Influenza: Recommendations of the Advisory Committee on Immunization Practices (ACIP)," *Morb. Mortal. Wkly. Rep.* 46 No. RR-9:1-25 and i-iv, United States Centers for Disease Control (1997).
Ichikawa, T., et al., "Geranylgeranylacetone Induces Antiviral Gene Expression in Human Hepatoma Cells," *BioChem. Biophys. Res. Commun.* 280:933-939, Academic Press (Jan. 2001).
Tytell, M. and Hooper, P.L., "Heat shock protein: new keys to the development of cytoprotective therapies," *Emerg. Ther. Targets* 5:267-287, Ashley Publications Ltd. (Apr. 2001).
Supplementary European Search Report for EP Application No. 02770261.2, mailed Nov. 28, 2007, European Patent Office, The Netherlands (2007).

* cited by examiner

*Primary Examiner*—Stacy B. Chen
(74) *Attorney, Agent, or Firm*—Sterne, Kessler, Goldstein & Fox P.L.L.C.

(57) ABSTRACT

To provide a novel preventive and/or therapeutic agent against a virus, disclosed is a preventive and/or therapeutic agent against a viral infection containing geranyl-geranyl acetone as an active ingredient. Also, disclosed are inducers for increasing the activity of an anitiviral factor and for protein kinase containing geranyl-geranyl acetone as an active ingredient. Moreover, a method for preventing and/or treating a viral infection which contains administering a patient a effective amount of an agent containing geranyl-geranyl acetone as an active ingredient.

1 Claim, 13 Drawing Sheets

METHOD OF TREATING INFLUENZA WITH GERANYL-GERANYL ACETONE

This application is a 371 national stage filing of PCT/JP02/11060, filed Oct. 24, 2002.

TECHNICAL FIELD

The present invention relates to a new use of geranyl-geranyl acetone as a preventive and/or therapeutic agent, and more particularly to the preventive and/or therapeutic agents for viral infection containing geranyl-geranyl acetone as an active ingredient.

BACKGROUND ART

Viruses cause a variety of illnesses. For example, influenza A viral infection involves one type of virus that causes group infection and epidemics around the world, and that often presents severe conditions for children, the elderly, and persons with cardiopulmonary diseases or immunodeficiency. (Refer to non-patent literatures 1 to 3.).

No reliable and effective remedy for viruses has yet been discovered during the development in recent years of various drugs. Currently, although inoculation with inactive vaccine has been used as an effective means, the influenza A virus, for example, has effectively altered its superficial antigenicity, and the therapeutic effectiveness of the vaccine is often reduced.

There have been many recent reports on the in vivo or in vitro effectiveness of chemotherapy on viral infections when using the new drugs zanamivir and oseltamivir (Refer to Non-Patent Literature 4 through 8.), which are neuraminidase inhibitors, as well as drugs such as amantazine and rimantadine, which are ion channel blockers.

However, there have been reports (Refer to Non-Patent Literature 9.) that these are only effective when administered during early infection, and cannot prevent pneumonia and secondary infection, and resistant viruses have been reported.

In this regard, heat shock protein (hereinafter referred to "HSP") belongs to the group of stress proteins induced in the cell under various kinds of stress, and the most notable phenomenon in this area is a heat shock protein with a molecular weight of 70 kD (hereinafter referred to "HSP70"). Recently, a wealth of research has focused on this topic, and there have been many reports of the protective effects of heat shock protein in relation to the living body and cells.

HSP has an anti-inflammatory action in relation to lipopolysaccharides, suppresses inflammatory cytokine, has an effect to protect from ischemia, and suppresses cellular apoptosis, therefore, from the perspective of protecting the body from attack, HSP shows promise for treating a variety of diseases such as septic shock, and ischemic conditions of vital organs such as the heart and brain.

However, there is no practical method to induce HSP for clinical applications, since the induction is based on the environmental stress such as heat shock, sodium arsenate and heavy metals, or on the disease stress such as ischemia. No method to safety induce HSP in the body has yet been established.

In recent years, there have been reports that the mechanism of action of geranyl-geranyl acetone (hereinafter referred to "GGA". Product name "Selbex", manufactured by Eisai Co., Ltd.) is mediated through the induction and expression of HSP. (Refer to Non-Patent Literature 10.) For this reason, GGA is gaining notable attention as a clinically applicable HSP inducer.

Thus, an object of the present invention is to provide a new drug for viruses by focusing on the strong HSP inductive action of GGA, and by studying the infection preventive and therapeutic effects in relation to viruses.

| | |
|---|---|
| Non-Patent Literature 1: | Glezen WP. Epidemiol Rev. 1982; 4: 25-44; |
| Non-Patent Literature 2: | Couch RB, Kasel JA, Glezen WP, et al. J. Infect Dis. 1986; 153: 431-40; |
| Non-Patent Literature 3: | MMWR Morb Mortal Wkly Rep 1997; 46(RR-9); 1-25; |
| Non-Patent Literature 4: | Woods JM, Bethell RC, Coates JA, et al. Antimicrob Agents Chemother 1993; 37: 1473-9; |
| Non-Patent Literature 5: | Hayden FG, Osterhaus ADME, Treanor JJ, et al. N Engl J Med 1997; 337: 874-80; |
| Non-Patent Literature 6: | Gubareva LV, Kaiser L, Hayden FG, Lancet 2000; 355(9206), 827-35; |
| Non-Patent Literature 7: | Long JK, Mossad, Goldman MP, Cleve Clin J Med 2000; 67: 92-5; |
| Non-Patent Literature 8: | Wingfield WL, Pollack D, Grunert RR, N Engli J Med 1969; 281: 579-84; |
| Non-Patent Literature 9: | Wingfield WL, Pollack D, Grunert RR, N Engli J Med 1969; 281: 579-84; |
| Non-Patent Literature 10: | Hirakawa T, Rokutan K, Nikawa T, et al. Gastroenterogy 1996; 111: 345-57. |

DISCLOSURE OF INVENTION

The above object is achieved by a preventive and/or therapeutic agent for a viral infection comprising geranyl-geranyl acetone as an active ingredient.

In a preferable aspect of the present invention, according to the aforementioned preventive and/or therapeutic agent for viral infection, the viral infection is influenza viral infection.

The aforementioned object is also achieved by a preventive and/or treatment method for viral infection comprising administering to a patient an effective amount of a drug comprising geranyl-geranyl acetone as an active ingredient.

The aforementioned object is also achieved by use of geranyl-geranyl acetone for the manufacture of a preventive and/or therapeutic agent for viral infection.

Further, the aforementioned object is achieved by an antiviral factor activity enhancer comprising geranyl-geranyl acetone as an active ingredient.

In a preferable aspect of the present invention, according to the antiviral factor activity enhancer, the antiviral factor is MxA.

Moreover, the aforementioned object is achieved by a protein kinase inducer comprising geranyl-geranyl acetone as an active ingredient.

In a preferable form of the present invention, according to the protein kinase inducer, the protein is an interferon-inducible double-stranded RNA activated protein.

According to the present invention, GGA has the effect of preventing viral infection when pre-administered prior to infection by a virus, and has the effect of treating viral infection when administered after infection.

In addition, according to the present invention, administration of GGA results in an increase of the expression of MxA, which is an antiviral gene, and results in an increase of the mRNA expression of interferon-inducible double-stranded RNA activated protein kinase.

BEST MODE FOR CARRYING OUT THE INVENTION

Figure 1:
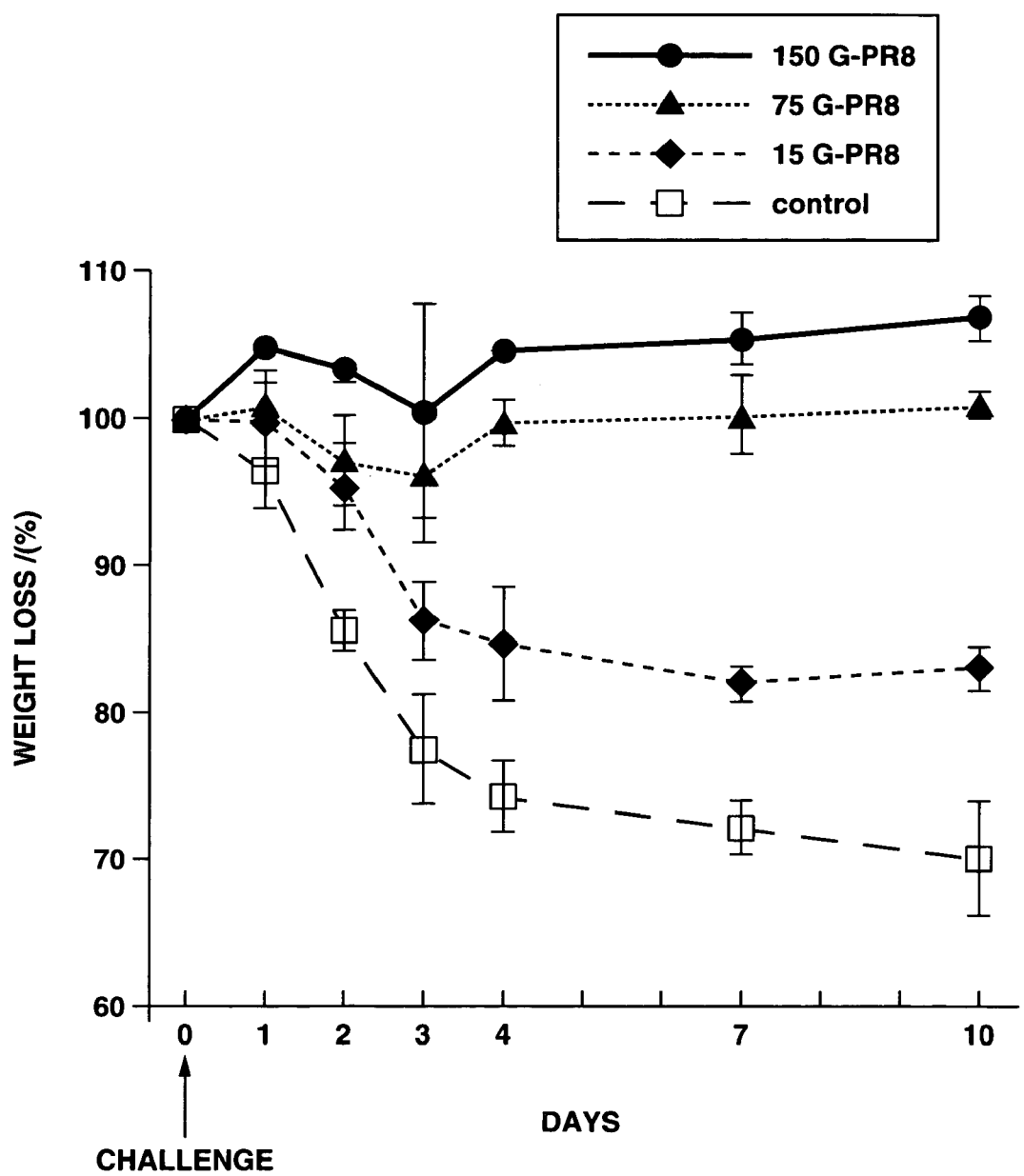
FIG. 1 indicates an improvement trend of clinical infection symptoms caused by administration of GGA in a mouse PR8 infection model according to the present invention. BALC/c mice that used in the present invention were randomly allotted into the following 4 groups: ① Control group (n=30) is transnasally administered $2\times10^5$ PFU of A/PR/8/34; the GGA pre-treatment groups were orally administered GGA every 12 hours for 3 weeks in doses of: ② 150 mg/kg (150G-PR8 group; n=30), ③ 75 mg/kg (75G-PR8 group; n=30), ④ 15 mg/kg (15G-PR8 group; n=30) and were infected with PR8 after 3 weeks in the same manner. The body weights of the mice were measured 1, 2, 3, 4, 7, and 10 days after infection.

The present invention discovers firstly that administration of GGA has an effect to prevent and treat infection by influenza viruses. The embodiment of the present invention will be described in detail below while explaining experiments conducted using the present invention.

The GGA used in the present invention has the generic name of teprenone, and is widely used as a drug to treat stomach ulcers and stomach inflammation; it is also possible to acquire GGA as a reagent or industrial raw material, and it can be synthesized using well-known methods of synthesis. The chemical name of GGA is 6, 10, 14, 18-tetramethyl-5, 9, 13, 17-nonadecatetraen-2-one, and the structural formula is as follows:

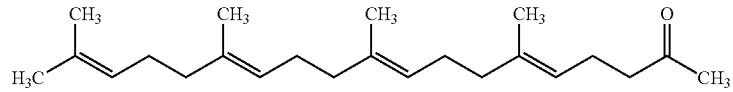

GGA has a double bond in 4 locations in its structure, and there are a total of 8 geometric isomers. However, the present invention is not particularly limited to one, and any one, or compounds of two or more, of the isomers may be used. (5E, 9E, 13E)-6, 10, 14, 18-tetramethyl-5, 9, 13, 17-nonadecatetraen-2-one, and (5Z, 9E, 13E)-6, 10, 14, 18-tetramethyl-5, 9, 13, 17-nonadecatetraen-2-one may be cited as preferable compounds among these.

In the present invention, mouse infection models were used as in vivo tests to study the trends in improving clinical infection symptoms, etc by administration of GGA. Specifically, groups are divided into a GGA pre-treatment group and a group without pre-treatment, and after infecting both groups with influenza virus, various types of behavior were observed in detail.

Further, influenza virus is used as a representative example of a virus, but the present invention is not limited to this, and includes viruses that cause flu such as the rhinovirus, and viruses that infect the skin and mucous membranes such as the herpes virus, etc.

After infection by an influenza virus, the effects of administering GGA are analyzed using well-known methods such as plaque assay, western blot, and northern blot from the perspective of the weights of the mice, viral replication in the lungs of the mice, viral nucleoprotein synthesis in the lungs of the mice, and expression of HSP70.

According to the previously described analyses, reduced weight loss in the mice, the reduction of the viral count in the lungs of the mice, the suppression of the amount of expression of virus nucleoprotein in the lungs of the mice, and the increased expression of HSP70 all indicates dependence on the concentration of GGA used for pre-treatment. Specifically, according to the present invention, the greater the dose of GGA in the group of mice pre-administered GGA, the less weight loss, and the results of finding no viral growth in the lungs indicate that it is possible to prevent viral infection by administering GGA in advance.

Next, in the present invention, human lung epithelial cells is used in in vitro experiments to study the presence of antiviral activity caused by administration of GGA.

Using A549 cells as the previously described human lung epithelial cells, the effect of GGA treatment to induce HSP, the synthesis capacity of nucleoproteins or HSP after infection by an influenza virus, and the expression of antiviral genes are assessed.

When treating with GGA according to the present invention, the expression of HSP70 mRNA is induced in a manner dependent on the concentration of GGA, and the synthesis capacity increases even at the level of protein material.

Even after infection with an influenza virus, GGA treatment causes strong expression of the HSP protein, and therefore, suppresses the capacity to synthesize various types of viral proteins such as influenza blood coagulant protein, matrix protein and non-structural protein.

Further, in the present invention, from studying the effects on the expression of anti-virus genes during infection with an influenza virus after GGA treatment, the expression of HSP70 mRNA is enhanced, and the expressions of MxA, which is an antiviral gene, and interferon-inducible double-stranded RNA activated protein kinase, which has an antiviral action, is activated in A549 cells treated with GGA. Thus, this suggests the possibility that the present invention has an enhanced biological function to prevent and suppress viral infection in host cells, and it may be inferred that the administration of GGA after viral infection has the effect of treating viral infection.

Here, the dose of GGA could be suitably determined based on the type of viral infection, symptoms, age, and body weight. Normally, the daily dose for adults is from 150 mg to 3 g, and preferably, from 200 mg to 2 g, and more preferably, from 250 mg to 1.5 g.

The method of administering GGA is not particularly limited, and oral or non-oral administration can be suitably selected, but oral administration is more preferable.

The form for oral administration may be a solid or liquid formulation, and specifically, a tablet, a coated tablet, a pill, a subtle granule, a granule, a powder, a capsule, a syrup, a emulsion, and a suspension are preferable. GGA is already widely used as a drug; the toxicity is low; there are no known side effects. Thus, it is a highly safe compound. Therefore, it may be orally administered as a powder. Alternatively, it may be made into a suitable formulation containing the additives most commonly used in the field of formulation (for example, lactose, sucrose, starch, mannitol, etc.) and thinners, etc.

Further, according to need, the aforementioned drug may be administered as a drug containing, in addition to GGA, an antioxidant, a binder (for example, α-starches, gum arabic, carboxymethyl cellulose, polyvinylpyrrolidone, and hydroxypropyl cellulose, etc.), a disintegrating agent (for example, calcium carbonate, and calcium carboxymethyl cellulose, etc.), a lubricant (for example, talc, magnesium stearate, and polyethylene glycol 6000, etc.), a colorant, a flavoring agent, and a fragrance, etc.

A preferable form of the preparation for non-oral administration include an injectable solution, a drip infusion preparation, an external preparation, and a suppository.

EXAMPLES

A further detailed description of the present invention will be provided below by indicating examples, but the present invention is not limited to these.

Further, the following experimental procedures relating to the handling of test animals were conducted with the approval of the Animal Testing Ethical Standards Committee of Oita Medical College.

The action of GGA in relation to the symptoms of viral infection, specifically, the infection rate and the death rate, in infection by a notable influenza virus was analyzed for in vivo and in vitro tests.

The virus used in the present invention was the influenza A virus, A/PR/8/34 (H1 N1) strain (hereinafter referred to "PR8"); the mice were 6-week old female SPF (specific pathogen-free) BALB/cN mice (Charles River Japan Co., Ltd.); and the cells were A549 cells derived from human alveolar epithelial cell.

First, the aforementioned mice were raised in a cage for each 4 mice under clean conditions and allowed free access to sterilized feed and water.

The mice were randomly divided into the following 4 treatment groups, and tested: ① Control group; intranasl infection with PR8 ($2 \times 10^5$ PFU) ② 150G-PR8; group; after administration of 150 mg/kg of GGA, infected with the same amount of PR8 in the same manner as the control group; ③ 75G-PR8 group; after administration of 75 mg/kg of GGA, infected with the same amount of PR8 in the same manner as the control group; ④ 15G-PR8 group; after administration of 15 mg/kg of GGA, infected with the same amount of PR8 in the same manner as the control group. The aforementioned group ① refers to the control group, and groups ② to ④ refer to the GGA treated group prior to infection. The GGA treated groups were orally administered GGA every 12 hours for 3 weeks.

FIG. 1 indicates the results of the effects of GGA on weight loss caused by PR8 infection. In the mouse PR8 infection model, the following observations were made regarding the improvement of the clinical symptoms of infection based on the administration of GGA.

In the control group, weight loss reaching 30% was observed after infection. In contrast, in the GGA treated groups, except for the 75G-PR8 group, almost no weight loss caused by infection was observed.

Figure 2:
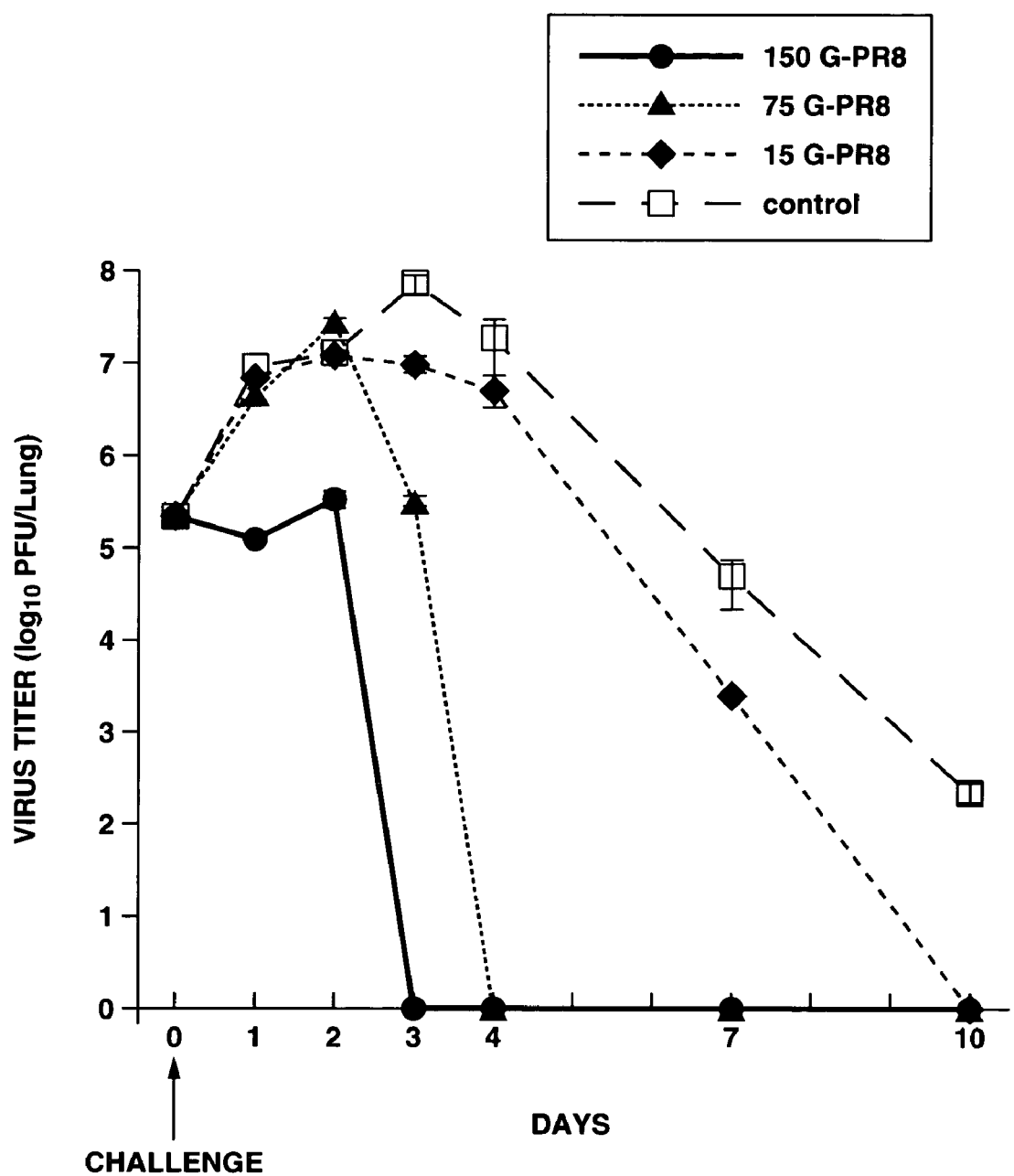
FIG. 2 indicates the effects of GGA on viral replication in the lungs of the mice of the various groups after infection by influenza viruses according to the present invention.

FIG. 2 indicates the effects of GGA on viral replication in the lungs of the mice of the various groups after infection by an influenza virus according to the present invention. Here, the assay of virus in the lung was conducted by plaque assay using MDCK. As can be seen in FIG. 2, the amount of PR8 virus in the lungs of the control group grew up to approximately $10^3$ times the amount of virus after initially being infected. On the other hand, the growth of virus in the lungs of the GGA treated groups was suppressed in a GGA dose-dependent manner, and the virus was completely eliminated after 3 days in the 150G-PR8 group, and after 4 days in the 75G-PR8 group.

Figure 3:
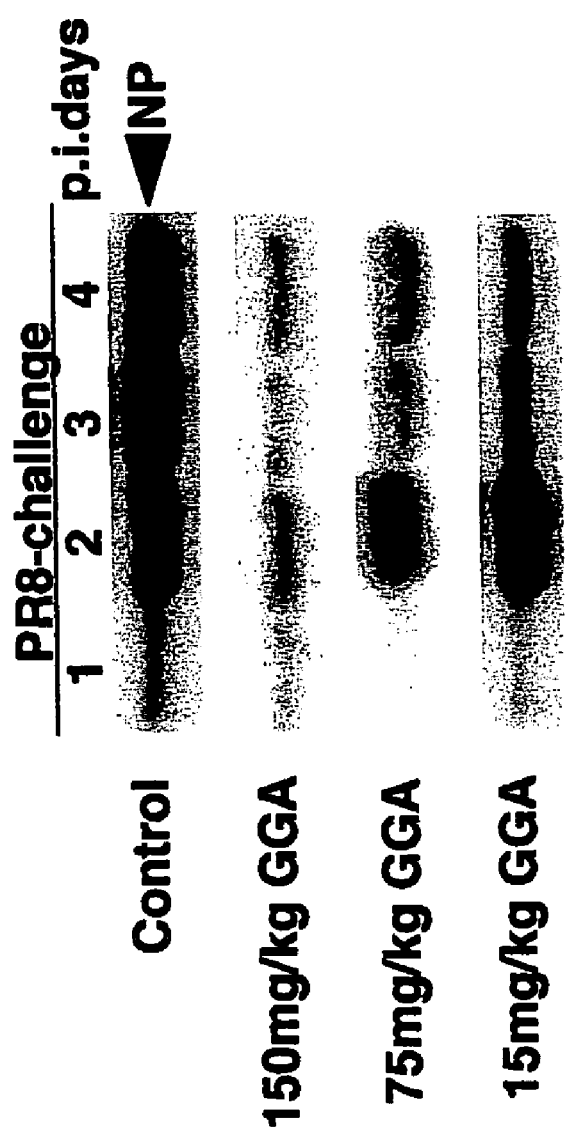
FIG. 3 indicates the effects of GGA on viral nucleoprotein synthesis in the lungs of mice in the various groups after infection by an influenza virus according to the present invention. Further, the 150 mg/kg GGA, 75 mg/kg GGA, and 15 mg/kg GGA in FIG. 3 indicate the 150G-PR8 group, 75G-PR8 group and 15G-PR8 group respectively.

FIG. 3 indicates the results of the effects of GGA on viral nucleoprotein (called "NP" hereinafter) synthesis in the lungs of the mice of the various groups after infection by an influenza virus according to the present invention. The amount of NP synthesis was measured with Western blot analysis. Compared with the control group, GGA treated groups were observed to exhibit suppression of NP synthesis in a dose dependent manner. The p.i. day listed in FIG. 3 indicates the number of days post-infection by PR8.

Figure 4:
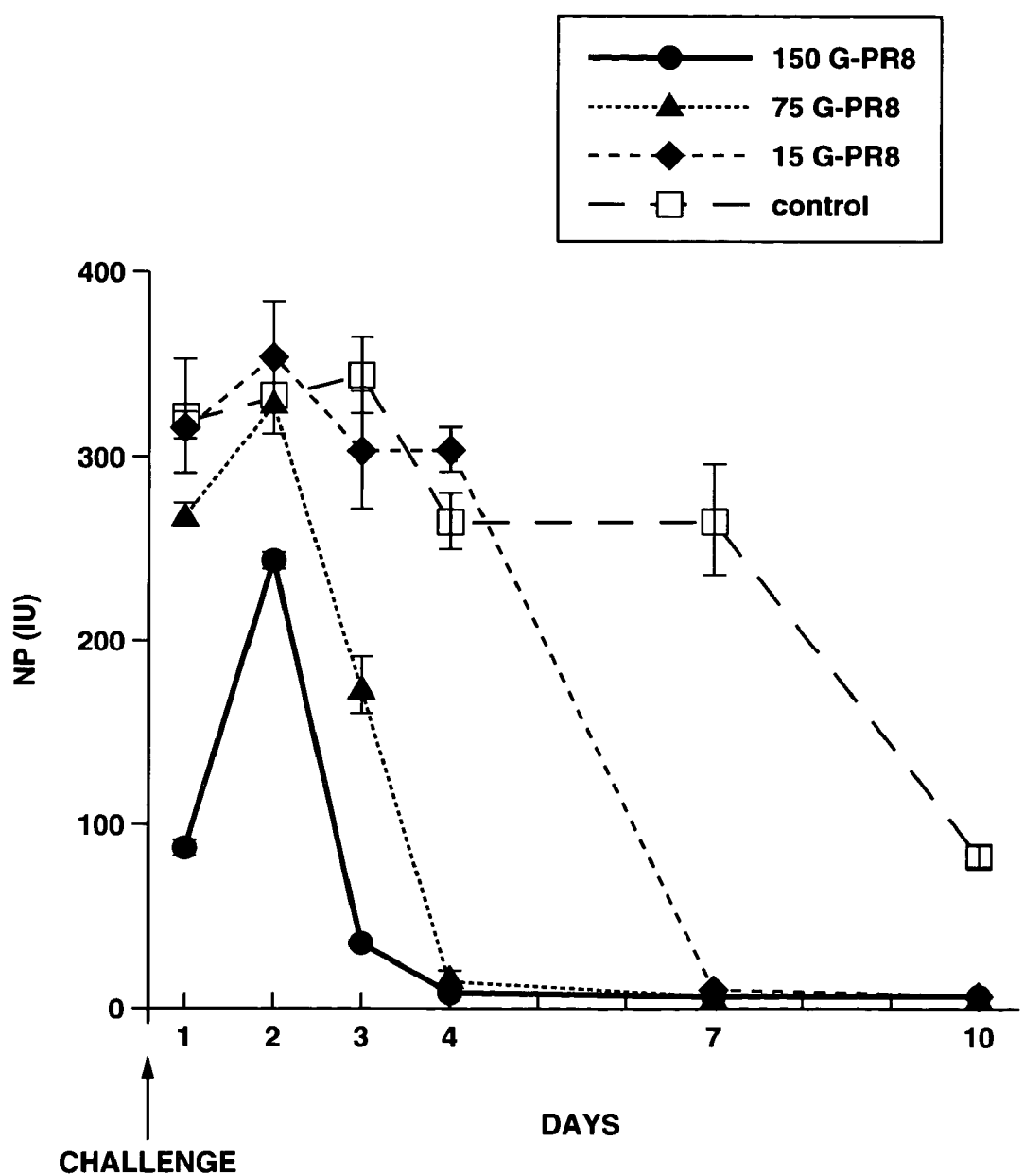
FIG. 4 indicates the effects of GGA on viral nucleoprotein synthesis in the lungs of mice in the various groups after infection by PR8 according to the present invention, and the results of assay using EIA.

FIG. 4 indicates the effects of GGA on viral NP synthesis in the lungs of the mice of the various groups after infection according to the present invention; and the results of conducting detailed assays using EIA are also indicated. As can be evident in FIG. 4, compared with the control group, which was not administered GGA, the capacity to synthesize NP after infection with PR8 was notably reduced in the GGA treated groups.

Next, it was confirmed whether or not GGA induced expression of HSP70 mRNA in the lungs of the mice.

Figure 5:
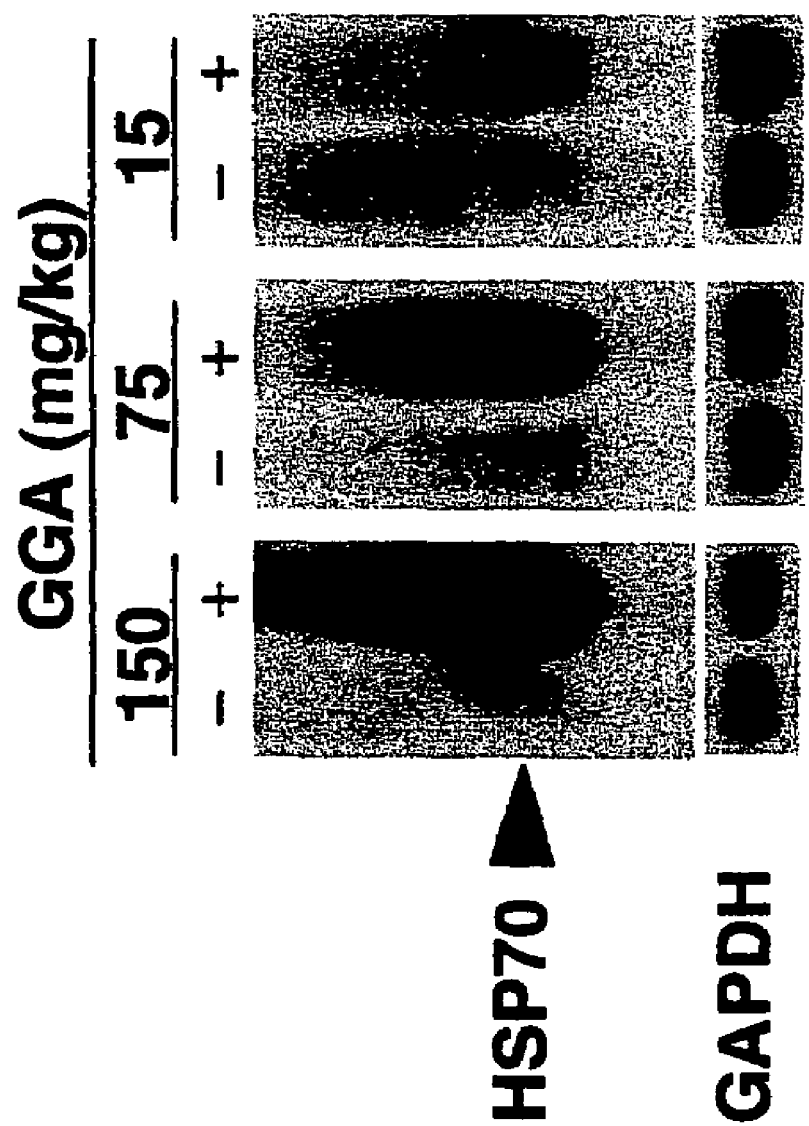
FIG. 5 indicates the results of expressing HSP70 in the lungs of mice administered GGA according to the present invention.

FIG. 5 indicates the expression of HSP70 in mice lungs induced by GGA. As is clear form FIG. 5, when administering GGA to BALB/c mice for 3 weeks (GGA150 in FIG. 5 indicates that 150 mg/kg of GGA was administered every 12 hours for 3 weeks), northern blot assay reveals that expression of HSP70 in the lungs was induced in a dose dependent manner. Specifically, GGA treated groups induced HSP70 more than the control group (corresponding to "−" in FIG. 5), and the greater the dose of GGA, the larger the amount of expression thereof.

Figure 6:
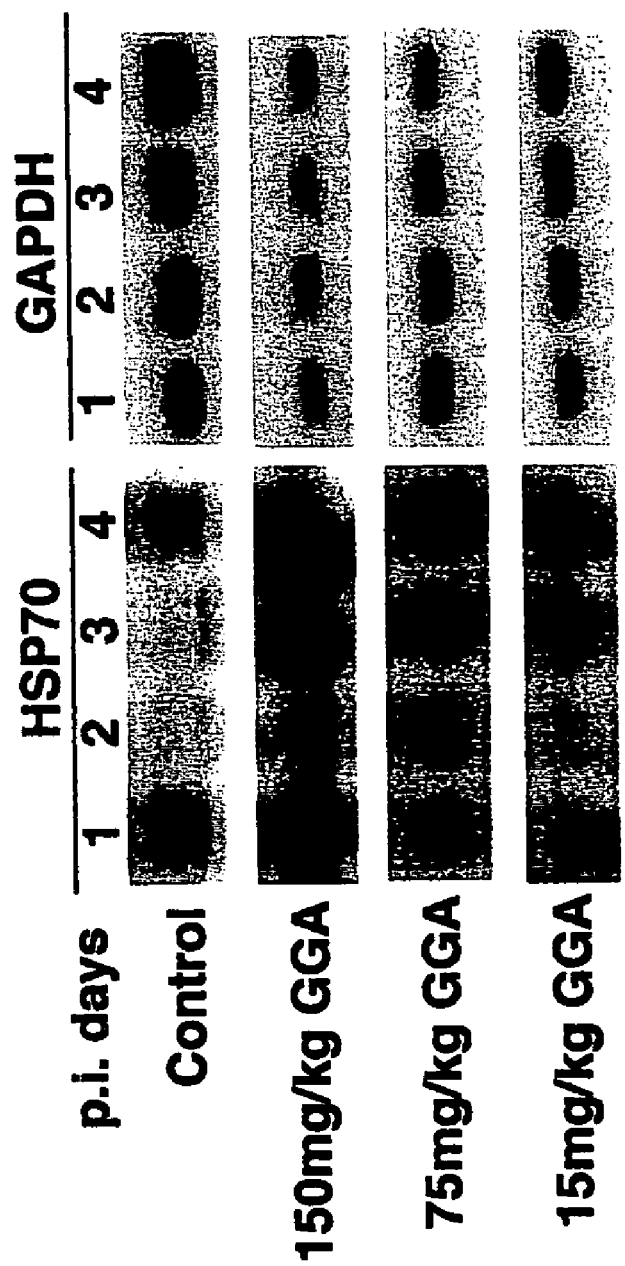
FIG. 6 indicates the effects of GGA on the dynamics of HSP70 mRNA expression in the lungs of mice after infection by PR8 according to the present invention, and the results of northern blot assessment. Further, the 150 mg/kg GGA, 75 mg/kg GGA, and 15 mg/kg GGA in FIG. 6 indicate the 150G-PR8 group, 75G-PR8 group and 15G-PR8 group respectively.

FIG. 6 indicates the results of using northern blot to study the effects of GGA on the dynamics of HSP70 mRNA expression in the lungs of mice after infection. In the same manner as in FIG. 5, FIG. 6 reveals that the amount of HSP70 expressed was dependent on the amount of GGA administered. Further, the p.i. day listed in FIG. 6 means the number of days post-infection by PR8.

FIGS. 5 and 6 are diagrams indicating the results of the expression of HSP70 in the lungs of the mice induced by administration of GGA when using glutaraldehyde diphosphate dehydrogenase (GAPDH) as a control. In FIG. 5, a vehicle was administered using a diluent containing α-tocopherol in an amount equivalent to that of the various doses.

The results of FIGS. 5 and 6 reveal that the administration of GGA alone caused expression of HSP70 mRNA in the lung tissues in a dose dependent manner; that compared with the control group after infection, the expression of HSP70 mRNA in the lungs of the GGA treated groups increased in agreement with the weight loss and viral reproduction periods in FIGS. 1 and 2; and that the enhancement of expression agreed with times of improvement in symptoms. This suggests that there is a strong correlative relationship between the expression of HSP70 and the suppression of the influenza infection.

The analysis of in vivo tests is explained above, and now the results of tests conducted in vitro will be explained below.

Figure 7:
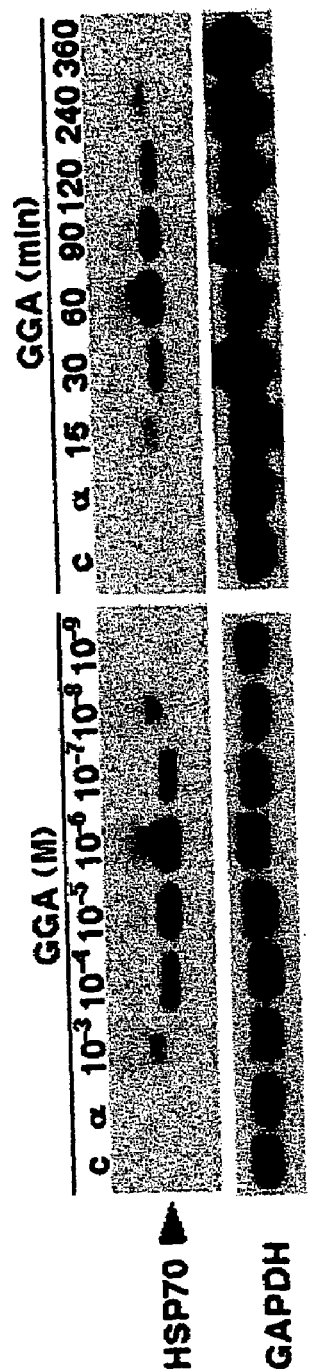
FIG. 7 indicates the effects of GGA on HSP induction in A549 cells derived from human lung epithelium, according to the present invention.

FIG. 7 indicates the results of treating A549 cells with GGA in in vitro tests conducted according to the present invention. Specifically, the results indicated in FIG. 7 reveal that GGA has an HSP inductive effect in A549 cells derived from human lung epithelium. Further, an assay of HSP induction was conducted using the northern blot method.

As indicated in FIG. 7, in the same way as in vivo, when GAPDH was controlled, the expression of HSP70 mRNA was induced in a concentration and time dependent manner. Incidentally, α in FIG. 7 indicates α-Tocophenol.

Figure 8:
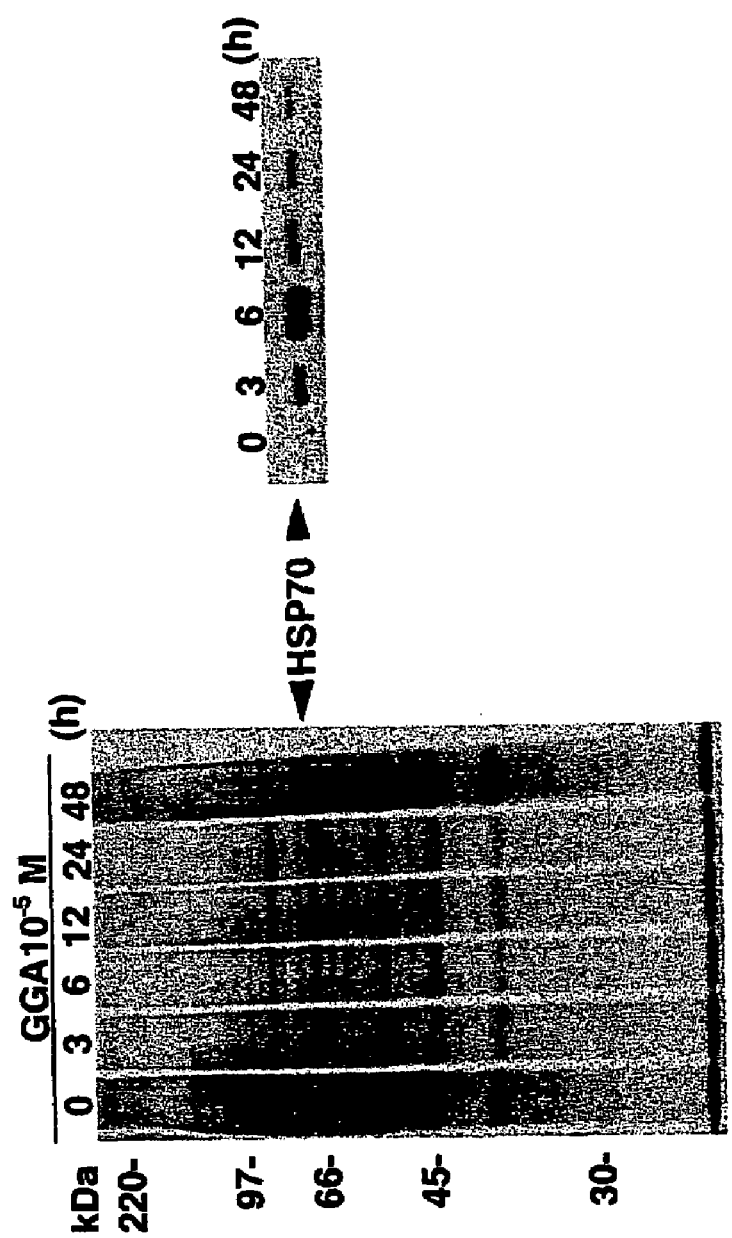
FIG. 8 indicates the results of using SDS-PAGE to develop intracellular protein based on pulse labeling using $^{35}$S-methionine in the present invention.

FIG. 8 indicates the results of using SDS-PAGE to develop intracellular protein based on pulse labeling using $^{35}S$-methionine. In these results, GGA powerfully induced the expression of approximately 70 kD proteins over 24 hours, and the capacity for synthesis at the level of protein material was notably elevated. (Refer to the left side of FIG. 8.) Moreover, when using western blot based on HSP70 antibodies to analyze the same samples, these proteins were identified as HSP70 (Refer to the right side of FIG. 8.), and the expression of HSP70 was measured as the peak of the expression 6 hours after administering GGA.

Figure 9:
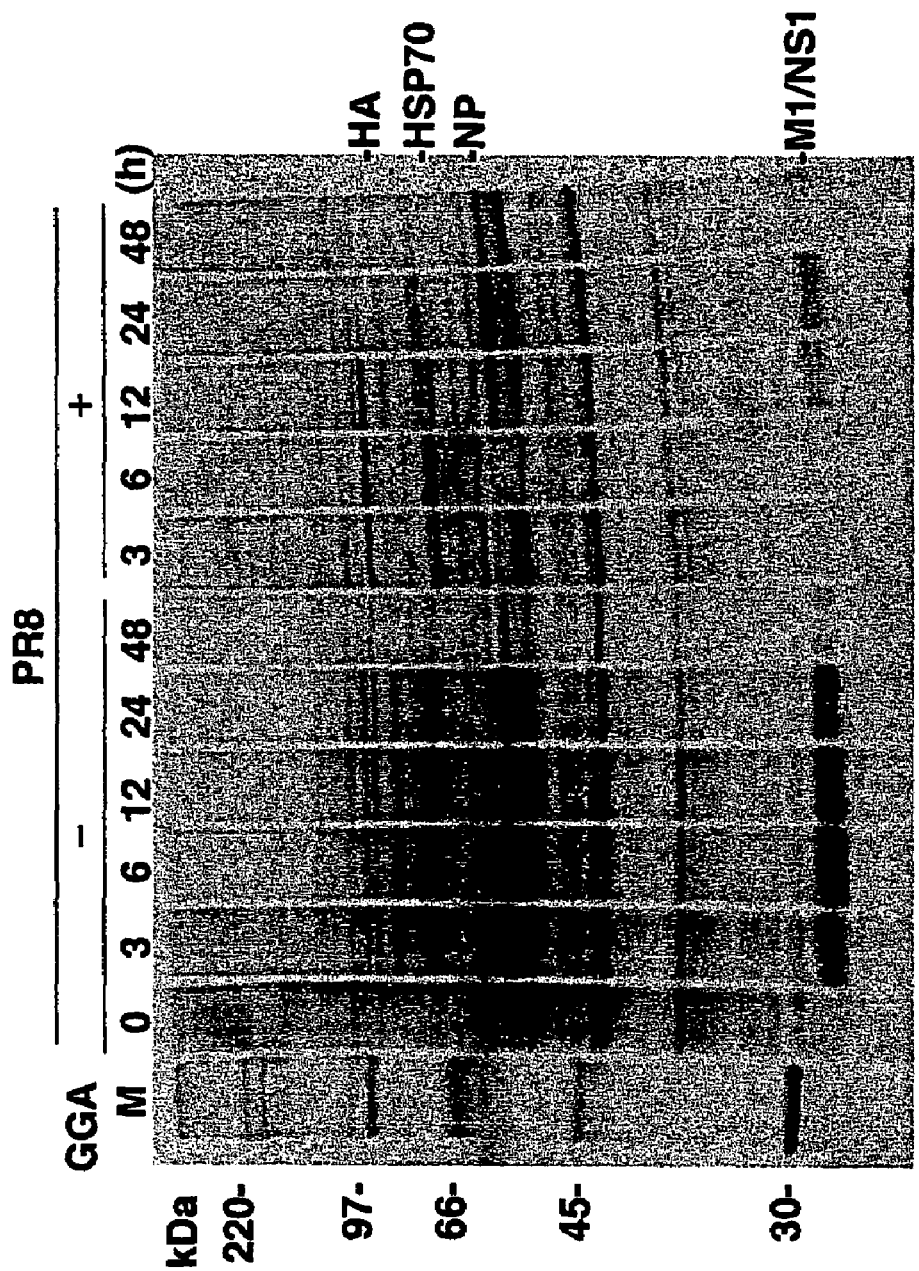
FIG. 9 indicates the results of studying the effects of GGA on NP and HSP70 synthesis capacities during PR8 infection according to the present invention.

FIG. 9 indicates the results of studying the effects of GGA on NP and HSP70 synthesis capacities during PR8 infection. The pulse labeling method was used to analyze the protein synthesis capacities of NP and HSP70 in A549 cells without GGA treatment (−) and in those with GGA treatment (+). In GGA treatment (−), the synthesis of NP was notably enhanced for 24 hours after infection. On the other hand, in GGA treatment (+), an enhancement of HSP70 synthesis was observed in the early period of infection, and synthesis of NP that matched a decline in HSP70 began after 12 hours. The synthesis capacity was suppressed compared to that of GGA treatment (−).

FIG. 9 also demonstrates that the capacity to synthesize viral proteins of PR8 such as HA (influenza hemagglutinin protein), NP, M1 (matrix protein), and NS1 (non-structural protein) was notably suppressed compared to the control. The suppression effect had a strong correlation with the time of expression of HSP70.

Figure 10:
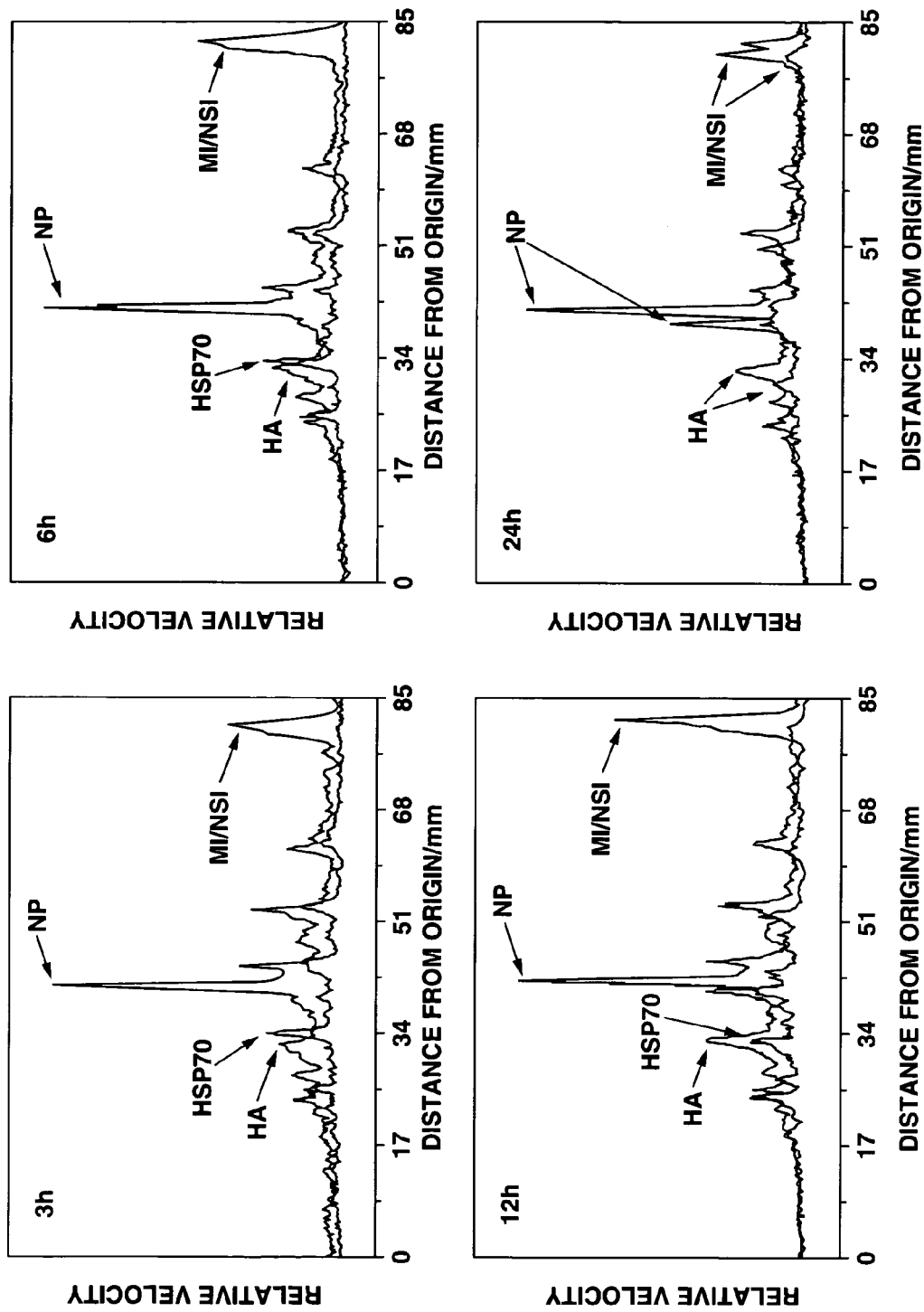
FIG. 10 indicates the results of densitometric analysis of the amount of protein in the samples studied in FIG. 9 at the various times after infection.

FIG. 10 indicates the results of densitometric analysis of the amount of protein in the samples studied in FIG. 9 at 3, 6, 12, and 24 hours after infection. The results of FIG. 10 reveal that HSP70 was expressed up to 12 hours after PR8 infection.

Figure 11:
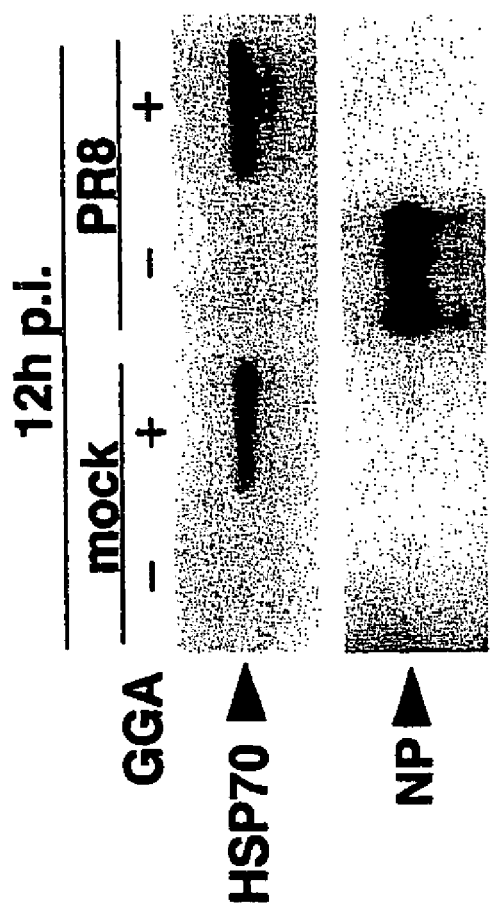
FIG. 11 indicates the results of western blot analysis of the accumulation of HSP70 and nucleoprotein NP in cells 12 hours after PR8 infection according to the present invention.

FIG. 11 indicates the results of western blot analysis of the accumulation of HSP70 and NP protein in cells 12 hours after PR8 infection according to the present invention. These results reveal no NP synthesis in the mock uninfected with virus. GGA treatment induced HSP70, the expression of NP was prevented up to 12 hours after infection, and viral protein synthesis was notably suppressed by synthesis of HSP70.

Figure 12:
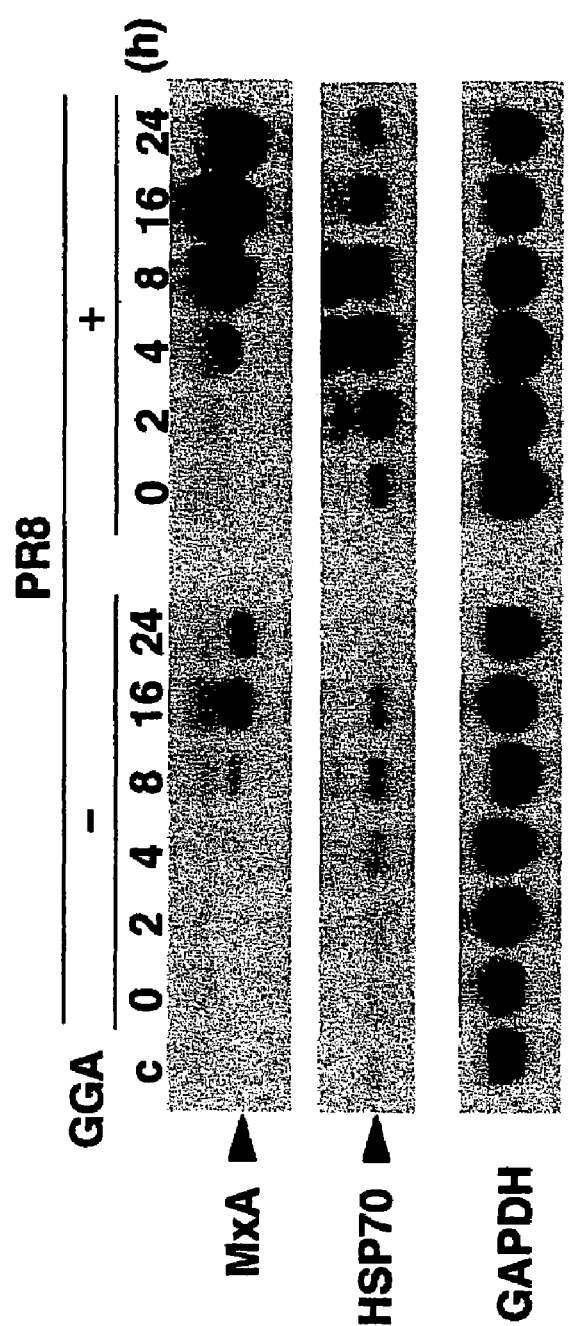
FIG. 12 indicates the effects of GGA treatment on the expression of anti-virus genes during PR8 infection according to the present invention.
Figure 13:
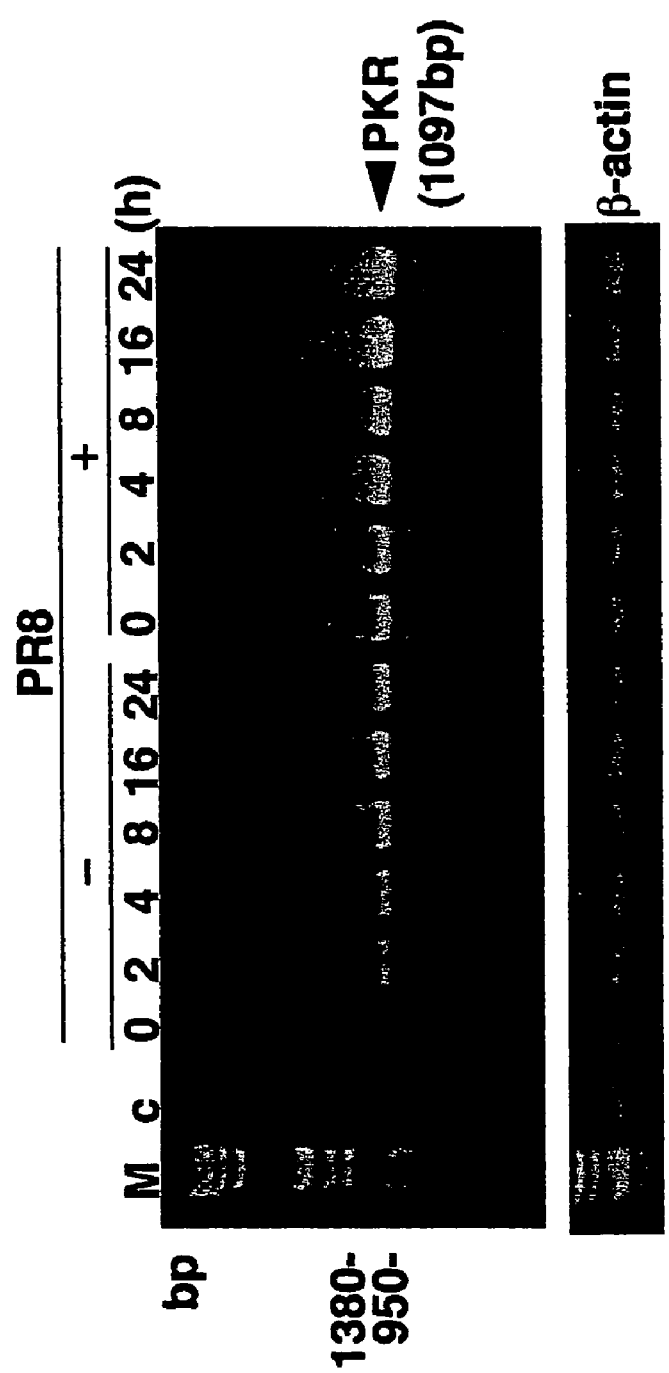
FIG. 13 indicates the effects of GGA treatment on the expression of anti-virus genes during PR8 infection according to the present invention.

Studied next were the effects of GGA treatment on the expression of antiviral genes after infection by PR8, and the results are indicated in FIGS. 12 and 13. In FIG. 12, northern blot analysis reveals that GGA treatment of A549 cells after infection with PR8 not only enhanced the expression of HSP mRNA, but also enhanced the expression of MxA genes, which are antiviral genes (specifically, orthomixovirus). It should be noted that the GAPDH in FIG. 12 was used as a control in the same way as previously described in FIG. 5.

FIG. 13 indicates the results of using RT-PCR to assay the mRNA expression of interferon-inducible double-stranded RNA activated protein kinase (hereinafter referred to "PKR"), which has an antiviral action. The results demonstrate that GGA treatment enhanced expression of PKR in A549 cells, and also up-regulates that mRNA. It should be noted that β-actin in this diagram was used was a control.

Generally, when viral infection occurs, the expression of a variety of genes, antiviral factors and enzymes in the body are enhanced or suppressed. From the perspective of mechanisms of action, the fact that GGA acting on MxA gene and PKR strongly suggests that GGA will be effective in the prevention and treating of viral infections, specifically, of influenza viruses. At the same time, it has been indicated that GGA is an antiviral factor activity enhancer or a protein kinase inducer.

The above results indicate that GGA exhibits an action to suppress growth of influenza viruses in vivo, and causes notable improvement of clinical symptoms such as weight loss. This suggests that GGA-induced HSP70 in the lungs deeply participates in that effect.

Moreover, it was demonstrated that GGA strongly induced expression of HSP70 in vitro, and that the period of this induction coincided with the inhibited replication of the influenza virus. Further, it was found that GGA activates host side antiviral gene MxA and PKR during viral infection, and enhanced the capacity of living bodies to prevent or suppress host viral infection. It was demonstrated that the administration of GGA is effective as prevention or as remedy for influenza viruses.

INDUSTRIAL APPLICABILITY

According to the above explanation, as a new use, geranyl-geranyl acetone may be applied as a preventive and/or therapeutic agent for viral infections.

We claim:

1. A method of treating an influenza virus infection, said method comprising administering to a patient an effective amount of a drug comprising geranyl-geranyl acetone as an active ingredient.

* * * * *